United States Patent [19]

Smigielski et al.

[11] Patent Number: 5,972,687
[45] Date of Patent: *Oct. 26, 1999

[54] **TOXIN GENE FROM *XENORHABDUS NEMATOPHILUS***

[75] Inventors: Adam Joseph Smigielski, O'Connor; Raymond Joseph Akhurst, Waramanga, both of Australia

[73] Assignee: Commonwealth Scientific and Industrial Research Organisation, Campbell, Australia

[*] Notice: This patent issued on a continued prosecution application filed under 37 CFR 1.53(d), and is subject to the twenty year patent term provisions of 35 U.S.C. 154(a)(2).

[21] Appl. No.: 08/569,168

[22] PCT Filed: Jun. 24, 1994

[86] PCT No.: PCT/AU94/00348

§ 371 Date: Apr. 5, 1996

§ 102(e) Date: Apr. 5, 1996

[87] PCT Pub. No.: WO95/00647

PCT Pub. Date: Jan. 5, 1995

[30]   Foreign Application Priority Data

Jun. 25, 1993 [AU] Australia ................................. PL9638

[51] Int. Cl.$^6$ ................ C12N 1/21; C12N 1/15; C12N 7/01
[52] U.S. Cl. .................... 435/252.3; 435/320.1; 435/252.33; 435/254.11; 536/23.1; 536/23.2; 536/23.7; 800/295; 800/302; 800/301; 935/9; 935/10; 935/22; 935/28; 935/31; 935/32; 935/38; 935/25; 935/64; 935/68; 935/72
[58] Field of Search ............................ 435/320.1, 172.3, 435/240.2, 240.21, 235.1, 254.11; 536/23.1, 23.2, 23.7; 800/2, 200, 230, DIG. 1, 6, 7, 9, 279–301, 302; 424/405, 93.1, 93.2

[56]   References Cited

FOREIGN PATENT DOCUMENTS

WO84/01775   5/1984   WIPO .

OTHER PUBLICATIONS

Weiss (May 30, 1997) Washington Post, p. A01.

Balcerzak et al., 1991, Acta Parasitol. Pol. 36(4): 175–181, in: Biol. Abstr. 94(1): AB–610, abstract 5707.

Jarosz et al., 1991, Entomophaga 36(3): 361–368, in: Biol. Abstr. 93(1): AB–610, abstract 5688.

Gaugler et al., eds., 1990, in: Entomopathogenic Nematodes in Biolgoical Control, CRC Press, Boca Raton, FL. pp. 76, 77, and 85.

B. V. McInerney et al. "Biologically Active Metabolites from Xenorhabdus SPP., Part 1. Dithiolopyrrolone Derivatives with antibiotic Activity" Journal of Natural Products (1991) 54:774–784.

B. V. McInerney et al. "Biologically Active Metabolites from Xenorhabdus SPP., Part 2. Benzopyran–1–one Derivatives with Gastroprotective Activity" Journal of Natural Products (1991) 54:784–795.

M.A. Innis et al. "PCR Protocols: A Guide to methods and Applications" Chapter 11 "Cloning with PCR" by S. J. Scharf pp. 84–91.

*Primary Examiner*—Christopher S. F. Low
*Attorney, Agent, or Firm*—McDermott, Will & Emery

[57]   ABSTRACT

Purified insecticidal toxins and biologically active fragments thereof, and polynucleotide molecules encoding same, from the bacteria *Xenorhabdus nematophilus* are described.

10 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 837 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ATGGTTATTA AACCCGTAAC AACTCCGAGT GTAATACAAT TAACGCCTGA TGATAGAGTA    60

ACGCCTGATG ATAAAGGTGA ATATCAACCC GTTGAAAAGC AAATAGCGGG AGATATAATA   120

CGTGTACTAG AATTCAAGCA AACAAATGAA AGTCATACAG GATTGTATGG AATTCCATAT   180

CGAGCTAAGA AAGTAATAAT AGCATATGCT TTAGCGGTAA GTGGTATTCA TAATGTCTCT   240

CAACTTCCAG AAGACTATTA TAAAAATAAG GATAACACAG GTAGAATTTA TCAAGTATAC   300

ATGTCTAATC TTTTATCTGC ACTATTGGGT GAGAATGGTG ATCAAATTTC TAAAGATATG   360

GCAAATGATT TTACCCAGAA CGAACTGGAG TTTGAGGTCA ACGTCTTAAA AATACCTGGG   420

ATATTCCTGA TCTTGAGAAT AAACTATTGG AAGATTTATT CAGATGAAGA TAAATTATTA   480

GCACTATATT TCTTTGCTTC ACAAGAACTT CCAATGGAGG CAAATCAACA ATCAAATGCA   540

GCAAATTTTT TTAAAGTAAT TGATTTTTTA CTTATCTTAT CTGCTGTAAC ATCACTGGGA   600

AAAAGGATTT TTTCAAAAAA TTTTTACAAT GGTCTAGAAA CTAAATCATT AGAGAATTAT   660

ATTGAGAGAA AAAAACTTTC TAAACCTTTC TTTCGACCAC CGCAGAAGTT ACCTGATGGC   720

AGAACAGGCT ACTTGGCCGG TCCAACAAAA GCGCCTAAAT TGCCAACAAC GTCTTCTACA   780

GCAACAACGT CTACAGCAGC TTCATCTAAT TGGAGAGTTA GTTTGCAAAA ACCTTAG      837
```

(2) INFORMATION FOR SEQ ID NO:2:

(i) SEQUENCE CHARACTERISTICS:
      (A) LENGTH: 278 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:2:

```
Met Val Ile Lys Pro Val Thr Thr Pro Ser Val Ile Gln Leu Thr Pro
 1               5                  10                  15

Asp Asp Arg Val Thr Pro Asp Asp Lys Gly Glu Tyr Gln Pro Val Glu
            20                  25                  30
```

```
Lys Gln Ile Ala Gly Asp Ile Ile Arg Val Leu Glu Phe Lys Gln Thr
            35                  40                  45

Asn Glu Ser His Thr Gly Leu Tyr Gly Ile Pro Tyr Arg Ala Lys Lys
    50                  55                  60

Val Ile Ile Ala Tyr Ala Leu Ala Val Ser Gly Ile His Asn Val Ser
65                  70                  75                  80

Gln Leu Pro Glu Asp Tyr Tyr Lys Asn Lys Asp Asn Thr Gly Arg Ile
                85                  90                  95

Tyr Gln Val Tyr Met Ser Asn Leu Leu Ser Ala Leu Leu Gly Glu Asn
                100                 105                 110

Gly Asp Gln Ile Ser Lys Asp Met Ala Asn Asp Phe Thr Gln Asn Glu
            115                 120                 125

Leu Glu Phe Glu Val Asn Val Leu Lys Ile Pro Gly Ile Phe Leu Ile
130                 135                 140

Leu Arg Ile Asn Tyr Trp Lys Ile Tyr Ser Asp Glu Asp Lys Leu Leu
145                 150                 155                 160

Ala Leu Tyr Phe Phe Ala Ser Gln Glu Leu Pro Met Glu Ala Asn Gln
                165                 170                 175

Gln Ser Asn Ala Ala Asn Phe Phe Lys Val Ile Asp Phe Leu Leu Ile
                180                 185                 190

Leu Ser Ala Val Thr Ser Leu Gly Lys Arg Ile Phe Ser Lys Asn Phe
            195                 200                 205

Tyr Asn Gly Leu Glu Thr Lys Ser Leu Glu Asn Tyr Ile Glu Arg Lys
210                 215                 220

Lys Leu Ser Lys Pro Phe Phe Arg Pro Pro Gln Lys Leu Pro Asp Gly
225                 230                 235                 240

Arg Thr Gly Tyr Leu Ala Gly Pro Thr Lys Ala Pro Lys Leu Pro Thr
                245                 250                 255

Thr Ser Ser Thr Ala Thr Thr Ser Thr Ala Ala Ser Ser Asn Trp Arg
            260                 265                 270

Val Ser Leu Gln Lys Pro
            275
```

(2) INFORMATION FOR SEQ ID NO:3:

(i) SEQUENCE CHARACTERISTICS:
        (A) LENGTH: 834 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
ATGGTTATTA AACCCGTAAC AACTCCGAGT GTAATACAAT TAACGCCTGA TGATAGAGTA      60

ACGCCTGATG ATAAAGGTGA ATATCAACCC GTTGAAAAGC AAATAGCGGG AGATATAATA     120

CGTGTACTAG AATTCAAGCA AACAAATGAA AGTCATACAG GATTGTATGG AATTCCATAT     180

CGAGCTAAGA AAGTAATAAT AGCATATGCT TTAGCGGTAA GTGGTATTCA TAATGTCTCT     240

CAACTTCCAG AAGACTATTA TAAAAATAAG GATAACACAG GTAGAATTTA TCAAGTATAC     300

ATGTCTAATC TTTTATCTGC ACTATTGGGT GAGAATGGTG ATCAAATTTC TAAAGATATG     360

GCAAATGATT TTACCCAGAA CGAACTGGAG TTTGAGGTCA ACGTCTTAAA AATACCTGGG     420

ATATTCCTGA TCTTGAGAAT AAACTATTGG AAGATTTATT CAGATGAAGA TAAATTATTA     480

GCACTATATT TCTTTGCTTC ACAAGAACTT CCAATGGAGG CAAATCAACA ATCAAATGCA     540

GCAAATTTTT TTAAAGTAAT TGATTTTTTA CTTATCTTAT CTGCTGTAAC ATCACTGGGA     600
```

```
AAAAGGATTT TTTCAAAAAA TTTTTACAAT GGTCTAGAAA CTAAATCATT AGAGAATTAT    660

ATTGAGAGAA AAAAACTTTC TAAACCTTTC TTTCGACCAC CGCAGAAGTT ACCTGATGGC    720

AGAACAGGCT ACTTGGCCGG TCCAACAAAA GCGCCTAAAT TGCCAACAAC GTCTTCTACA    780

GCAACAACGT CTACAGCAGC TTCATCTAAT TGGAGAGTTA GTTTGCAAAA ACCT          834
```

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CCATCGATCA TATGGTTATT AAACC                                           25
```

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CGGGATCCTT ATCTCTAAGG TTTTT                                           25
```

(2) INFORMATION FOR SEQ ID NO:6:

(i) SEQUENCE CHARACTERISTICS:
        (A) LENGTH: 1272 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
AAGAAACCGT AACAGCGGAA ATCAACGCTG CAATTTATAT TAGTAGTCAT TTCAATAAAC     60

GCCAACATAA TGGGAAAGTA CAATGGTTAT TAAACCCGTA ACAACTCCGA GTGTAATACA    120

ATTAACGCCT GATGATAGAG TAACGCCTGA TGATAAAGGT GAATATCAAC CCGTTGAAAA    180

GCAAATAGCG GGAGATATAA TACGTGTACT AGAATTCAAG CAAACAAATG AAAGTCATAC    240

AGGATTGTAT GGAATTCCAT ATCGAGCTAA GAAAGTAATA ATAGCATATG CTTTAGCGGT    300

AAGTGGTATT CATAATGTCT CTCAACTTCC AGAAGACTAT TATAAAAATA AGGATAACAC    360

AGGTAGAATT TATCAAGTAT ACATGTCTAA TCTTTTATCT GCACTATTGG GTGAGAATGG    420

TGATCAAATT TCTAAAGATA TGGCAAATGA TTTTACCCAG AACGAACTGG AGTTTGAGGT    480

CAACGTCTTA AAAATACCTG GGATATTCCT GATCTTGAGA ATAAACTATT GGAAGATTTA    540

TTCAGATGAA GATAAATTAT TAGCACTATA TTTCTTTGCT TCACAAGAAC TTCCAATGGA    600

GGCAAATCAA CAATCAAATG CAGCAAATTT TTTTAAAGTA ATTGATTTTT TACTTATCTT    660

ATCTGCTGTA ACATCACTGG GAAAAAGGAT TTTTTCAAAA AATTTTTACA ATGGTCTAGA    720

AACTAAATCA TTAGAGAATT ATATTGAGAG AAAAAAACTT TCTAAACCTT TCTTTCGACC    780

ACCGCAGAAG TTACCTGATG GCAGAACAGG CTACTTGGCC GGTCCAACAA AAGCGCCTAA    840
```

-continued

```
ATTGCCAACA ACGTCTTCTA CAGCAACAAC GTCTACAGCA GCTTCATCTA ATTGGAGAGT      900

TAGTTTGCAA AAACCTTAGA GATAACCCAT CCAGAAATAC ATTTATGAAA ATGGATGATG      960

CTGCAAAACG AAAATATAGT TCATTTATAA AAGAGGTACA AAAGGGTAAT GATCCACGTG     1020

CAGCAGCAGC AAGTATTGGT ACAAAAAGCG GCAGTAACTT CGAAAAACTG CAAGGTAGAG     1080

ATTTATATAG TATAAGACTA AGCCAAGAAC ACAGGGTAAC ATTCTCCATA AATAATACTG     1140

ACCAAATAAT GGAGATCCAA AGTGTTGGAA CTCATTACCA AAATATATAA CCTGATTTAT     1200

AGTAGTGATA AGACGTAAGA TAAATATGGA AGGTTGTAAT TCTATTGCAC TTCCTCAGAG     1260

GTGACCGCTC AG                                                        1272
```

(2) INFORMATION FOR SEQ ID NO:7:

(i) SEQUENCE CHARACTERISTICS:
        (A) LENGTH: 383 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Met Val Ile Lys Pro Val Thr Thr Pro Ser Val Ile Gln Leu Thr Pro
 1               5                  10                  15

Asp Asp Arg Val Thr Pro Asp Lys Gly Glu Tyr Gln Pro Val Glu
            20                  25                  30

Lys Gln Ile Ala Gly Asp Ile Ile Arg Val Leu Glu Phe Lys Gln Thr
            35                  40                  45

Asn Glu Ser His Thr Gly Leu Tyr Gly Ile Pro Tyr Arg Ala Lys Lys
 50                  55                  60

Val Ile Ile Ala Tyr Ala Leu Ala Val Ser Gly Ile His Asn Val Ser
 65                  70                  75                  80

Gln Leu Pro Glu Asp Tyr Tyr Lys Asn Lys Asp Asn Thr Gly Arg Ile
            85                  90                  95

Tyr Gln Val Tyr Met Ser Asn Leu Leu Ser Ala Leu Leu Gly Glu Asn
           100                 105                 110

Gly Asp Gln Ile Ser Lys Asp Met Ala Asn Asp Phe Thr Gln Asn Glu
           115                 120                 125

Leu Glu Phe Glu Val Asn Val Leu Lys Ile Pro Gly Ile Phe Leu Ile
       130                 135                 140

Leu Arg Ile Asn Tyr Trp Lys Ile Tyr Ser Asp Glu Asp Lys Leu Leu
145                 150                 155                 160

Ala Leu Tyr Phe Phe Ala Ser Gln Glu Leu Pro Met Glu Ala Asn Gln
               165                 170                 175

Gln Ser Asn Ala Ala Asn Phe Phe Lys Val Ile Asp Phe Leu Leu Ile
           180                 185                 190

Leu Ser Ala Val Thr Ser Leu Gly Lys Arg Ile Phe Ser Lys Asn Phe
       195                 200                 205

Tyr Asn Gly Leu Glu Thr Lys Ser Leu Glu Asn Tyr Ile Glu Arg Lys
       210                 215                 220

Lys Leu Ser Lys Pro Phe Phe Arg Pro Pro Gln Lys Leu Pro Asp Gly
225                 230                 235                 240

Arg Thr Gly Tyr Leu Ala Gly Pro Thr Lys Ala Pro Lys Leu Pro Thr
               245                 250                 255

Thr Ser Ser Thr Ala Thr Thr Ser Thr Ala Ala Ser Ser Asn Trp Arg
           260                 265                 270
```

```
Val Ser Leu Gln Lys Pro Arg Pro Ile Gln Lys Tyr Ile Tyr Glu Asn
    275             280             285

Gly Cys Cys Lys Thr Lys Ile Phe Ile Tyr Lys Arg Gly Thr Lys Gly
    290             295             300

Ser Thr Cys Ser Ser Ser Lys Tyr Trp Tyr Lys Lys Arg Gln Leu Arg
305             310             315                     320

Lys Thr Ala Arg Arg Phe Ile Tyr Lys Thr Lys Pro Arg Thr Gln Gly
            325             330             335

Asn Ile Leu His Lys Tyr Pro Asn Asn Gly Asp Pro Lys Cys Trp Asn
            340             345             350

Ser Leu Pro Lys Tyr Ile Thr Phe Ile Val Val Ile Arg Arg Lys Ile
        355             360             365

Asn Met Glu Gly Cys Asn Ser Ile Ala Leu Pro Gln Arg Pro Leu
    370             375             380
```

TOXIN GENE FROM *XENORHABDUS NEMATOPHILUS*

This application is a filing under 35 U.S.C. 371 of PCT/AU94/00348 filed Jun. 24, 1994.

TECHNICAL FIELD

The present invention concerns the identification and isolation of a new class of protein toxins specific against insects which are produced by bacteria from the species *Xenorhabdus nematophilus* and possibly by the species *X.beddingii*. In addition, the present invention relates to the insertion of this class of toxin into recombinant viruses, bacteria, protozoa, fungi, and transgenic plants in order to broaden the use of these toxins for control of a large range of insect pests and plant parasitic nematodes.

BACKGROUND

Insect pathogenic nematodes of the family Steinernematidae are known to be symbiotically associated with bacteria of the genus Xenorhabdus. It has been observed that these bacteria have the ability to kill a wide range of different insects without the aid of their nematode partners.

The present inventors have identified a new class of toxins. A DNA fragment encoding one of these toxins has been isolated from *Xenorhabdus nematophilus* stain A24 and characterised by sequencing. As will be recogised by persons skilled in the art, DNA fragments encoding members of this new class of toxins may be usefully introduced into viral agents, including entomopox and nuclear polyhedrosis viruses; bacteria (including Gracilicutes, Firmicutes, Tenericutes and Mendosicutes); fungi; protozoa; and plants.

SUMMARY OF THE PRESENT INVENTION

In a first aspect, the present invention consists in a polynucleotide molecule comprising a nucleotide sequence which encodes an insecticidal toxin and which is at least 70% homologous to the nucleotide sequence shown in Table 1 from residue 83 to 919 (SEQ ID NO:1), or a fragment thereof which fragment encodes an insecticidal polypeptide.

In a preferred embodiment of the present invention the nucleotide sequence is at least 90% homologous to the sequence shown in Table 1 from residue 83 to 919 (SEQ ID NO:1).

Preferably, the nucleotide sequence which encodes an insecticidal toxin from Xenorhabdus and more preferably, the nucleotide sequence substantially corresponds to the sequence shown in Table 1 from residue 83 to 919 (SEQ ID NO:1).

In a second aspect the present invention provides an insecticidal toxin which includes an amino acid sequence which is at least 70% homologous to residues 1 to 278 (SEQ ID NO:2) shown in Table 2 or a functional fragment thereof.

In a preferred embodiment of the present invention the insecticidal toxin includes an amino acid sequence which is at least 90% homologous to residues 1 to 278 (SEQ ID NO:2) shown in Table 2 or a functional fragment thereof.

In a further preferred embodiment the insecticidal toxin includes an amino acid sequence substantially corresponding to residues 1 to 278 (SEQ ID NO:2) in Table 2 or a functional fragment thereof.

In a third aspect the present invention provides a recombinant organism, the organism being characterised in that it is transformed with the polynucleotide molecule of the first aspect of the present invention.

The organisms which may be usefully transformed with the polynucleotide molecule of the first aspect of the present invention include viral agents such as entomopox and nuclear polyhedrosis viruses; bacteria, such as Gracilicutes, Firmicutes, Tenericutes and Mendosicutes; fungi; protozoa; and plants.

The term "substantially corresponds" as used herein in relation to the nucleotide sequence is intended to encompass minor variations in the nucleotide sequence which due to degeneracy do not result in a change in the encoded protein. Further this term is intended to encompass other minor variations in the sequence which may be required to enhance expression in a particular system but in which the variations do not result in a decrease in biological activity of the encoded protein.

The term "substantially corresponding" is used herein in relation to the amino acid sequence is intended to encompass minor variations in the amino acid sequence which do not result in a decrease in biological activity of the insecticidal toxin. These variations may include conservative amino acid substitutions. The substitutions envisaged are:

G, A, V, I, L, M; D, E; N, Q; S, T; K, R, H; F, Y, W, H; and P, Nα-alkylamino acids.

As used herein the term "functional fragments" is intended to encompass fragments of the insecticidal toxin which retain insecticidal activity.

In a fourth aspect, the present invention provides a method for controlling the proliferation of insects, comprising applying to an infested area a recombinant organism according to the third aspect optionally in admixture with an acceptable agricultural carrier.

Isolation and Characterisation of a Toxin from *Xenorhabdus nematophilus* A24

Generation of a Cosmid Library

Genomic DNA from *Xenorhabdus nematophilus* A24, isolated using the method of Marmur (1961) was partially digested using the restriction enzyme Sau 3A, to generate fragments of DNA that were in the size range of 30 to 50 kilobasepairs (kb), and dephosphorylated using the enzyme calf alkaline phosphatase. The cosmid "Supercos" (Stratagene) was prepared to receive foreign insert DNA into its Bam HI cloning site according to the manufacturer's instructions. The digested DNA from *X.nematophilus* A24 was added to the cosmid DNA in a ratio of 3:1 and ligated together using the enzyme T4 DNA ligase. The ligated material was subsequently packaged into λ-bacteriophage using the Gigapack II XL Packaging Extract (Stratagene) as per the manufacturer's instructions. The packaged DNA was subsequently transfected into the Escherichia coli strain NM554 (F-, recA, araD139,Δ (ara, leu) 7696, Δlac Y74, galU-, galK-, hsr, hsm$^+$, strA, mcrA[-], mcrB[-]. Bacteria were plated out onto Luria Bertani (LB) agar plates containing 150 μg ml$^{-1}$ ampicillin to select for those bacteria containing recombinant Supercos plasmids.

Screening for Toxin Producing Clones

Individual clones were grown overnight at 28° C. in LB containing 150 μg ml$^{-1}$ ampicillin. Cultures were treated for 15 minutes with 2 mg ml$^{-1}$ lysozyme in order to release any proteins produced by the recombinant DNA into the medium. Five μl aliquots of this solution were then injected directly into the haemocoel of three *Galleria mellonella* fourth instar larvae. Appropriate controls containing lysozyme and non-recombinant *E.coli* NM554 cultures were also injected to confirm the absence of any toxicity to these larvae. Two clones were found to have strong insecticidal activity. Injected larvae were found to be very sluggish after 30 hours, with all larvae dead within three days.

Characterisation of Toxin Producing Clones

The recombinant Supercos DNA from these clones was isolated using an alkaline lysis procedure (Maniatis et al., 1982). Isolated DNA was digested with varying restriction enzymes and analysed using TAE agarose gel electrophoresis (Maniatis et al, 1982). It was found that both clones were identical and contained a 34.6 kb DNA insert from *X. nematophilus* A24. One of these clones cos149 was chosen for further study.

A 7.4 kb Bam HI fragment from cos149 was cloned into the plasmid vector pGEM7Z(f)+ (Promega) which was transformed into the *E.coli* strain DH5α (F−, Φ80dlac ZΔ M15, recA1, endA1, gyrA96, thi-1, hsdR17[$r_{K-}$, $m_{K+}$]sup E44, relA1, deoR, Δ[lacZYA-argF] U169) using electroporation at 25 μF, 200 Ω and 2.5 kV in a 0.2 cm cuvette in a Bio-Rad Gene Pulser. This clone (N8pGEM) was found to continue to be toxic against *G.mellonella* larvae.

Plasmid DNA from N8pGEM was isolated and digested with the restriction enzymes ClaI and SphI. This resulted in the linearization of this plasmid containing one end (3') which was resistant to digestion by the enzyme Exonuclease III and the other end (5') which could be digested at a constant rate of 450 bases per minute at 37° C. by this enzyme using the Erase-a-Base kit from Promega. Using this enzyme aliquots containing decreasing size plasmids were obtained which were recircularised using the enzyme T4 DNA ligase. Recircularised plasmids were reintroduced into the bacterium *E.coli* strain DH5α using electroporation (see above). Varying size clones were selected and used for injecting *G.mellonella* larvae. The smallest clone which continued to be insecticidal was found to contain 1.5 kb of *X.nematophilus* A24 DNA and was designated tox 1.

Plasmid DNA from tox 1 was isolated and digested with the restriction enzymes Sac I and HindIII, respectively to again create linear molecules with one end resistant and the other sensitive to digestion with Exonuclease III. Deletion mutants were isolated and tested against *G.mellonella* larvae. A clone which now only contained 1.2 kb of *X.nematophilus* A24 DNA was isolated and was toxic against our test insect. This clone was designated toxb4.

The recombinant plasmids from toxb4 and three further (non-toxic) deletion clones, toxb5, toxb6 and toxb7, were isolated and used for obtaining the sequence of both strands of the toxin gene. Sequencing was performed using the Applied Biosystems, Incorporated Model 370 automated sequencer. Sequencing templates were prepared using double stranded DNA templates and the 21M13 and SP6 primer sites located on the pGEM7Z(f)+ plasmid and using the Taq dye primer cycle sequencing protocol (Applied Biosystems, Incorporated).

The toxin gene was found to consist of an 834 basepair open reading frame (Table 1) (SEQ ID NO:3) which translates into a 278 amino acid protein (Table 2) (SEQ ID NO:2). The start of the toxin gene sequence was preceded by appropriate DNA promoters necessary for transcription of the gene into a mRNA molecule prior to its synthesis into a peptide. These consist of a Shine-Dalgarno poly-purine sequence and −10 and −35 RNA polymerase recognition sequences (Table 1).

The DNA sequence and the derived amino acid sequences were analysed by sequence data bank analyses to determine if any other related sequences have previously been identified. The results indicated that no other sequence exists in the GenBank and EMBL data banks which has any similarity to this gene and its product.

Cloning of Xenorhabdus Toxin into a High-Expression Vector

Using the determined DNA sequence, 20-mer DNA primers were designed to cover the 5' and 3' region of the toxin gene and thus allow PCR amplification of the toxin and subsequent insertion into an expression vector. These primers included linker regions containing appropriate restriction enzyme sites (ClaI and NdeI for the 5' primer and Bam HI for the 3' primer).

5' primer CCATCGATCATATGGTTATTAAACC (SEQ ID NO:4)

3' primer CGGGATCCTTATCTCTAAGGTTTTT (SEQ ID NO:5)

Utilising a standard PCR protocol (Innis, M. A., Gelford, D. H., Sminsky, J. J. and White, T. J.: (1990). PCR Protocols : A Guide to Methods and Applications. Academic Press, San Diego. 482pp) the toxin was amplified out of the genome of *X.nematophilus* A24 and restriction digested with Cla I and Bam HI. The digested fragment was subsequently ligated into pGEM-7Zf(+) and then subcloned from this vector into the high expression vector pT7T2b(derived from pET11 [Novagen] and carrying the T7 promoter upstream from the start of the toxin insert; constructed by Dr. Karl Gordon, CSIRO, Division of Entomology) using the restriction enzyme sites Nde I and Bam HI. The recombinant plasmid was transformed into the *E. coli* strain BL21(DE3) [F-ompT $r_B$ -$m_B$ -, which carries in its chromosome the T7 RNA polymerase gene under lac UV5 control). Induction of the toxin may be achieved by the addition of 0.4 mM IPTG at mid-exponential phase of the culture and continuing the incubation for an extra 4 hours.

In vitro expression of the 1.2 Kb insert fragment from toxb4 was achieved with the E.c. S30 Extract Procaryotic Translation System for linear DNA. Only a 30 kDa peptide was produced indicating that the 1.2 Kb fragment encodes one peptide only—the insect toxin.

Southern Blot Hybridization of a Range of Xenorhabdus species and Photohabdus Luminescens Strains with the *X.nematophilus* A24 Toxin Gene DNA isolated from a range of Xenorhabdus species and Photohabdus (bacteria symbiotically associated with nematodes from the family Heterohabditidae) controls was digested to completion with the restriction enzyme Eco RV and run out on a 0.8% TAE agarose gel and the DNA fragments blotted and fixed onto a Hybond-N+ membrane (Amersham) as per the manufacturer's instructions.

The toxin gene was radiolabelled with $^{32}$p using nick translation (Maniatis et al., 1982) and probed against the blot containing the DNA of a range of Xenorhabdus and Photohabdus strains (Maniatis et al., 1982). Under moderate stringency wash conditions at 65° C.(0.1% SDS, 1% SSPE, Maniatis et al, 1982) the toxin only hybridised to *X. nematophilus* and *X. beddingii* strains. However, the toxin gene did not show any homology to the DNA from strains of *X. bovienli, X. poinarii,* some unclassified Xenorhabdus spp. and *Photohabdus luminescens*. This result suggests that this toxin type is confined to strains from the species *X. nematophilus* and *X. beddingii*. As *X. beddingii* has insecticidal activity and shows homology to the toxin gene it is most probable that these sequences are part of related/similar yet slightly different toxins. A high stringency wash at 65° C.(0.1% SDS, 0.1% SSPE; Maniatis et al. 1982) of the blot removed the message from the *X.beddingii* strain, but not from the *X.nematophilus* strains.

Characteristics of the Toxic Protein Product

The toxin is inactivated by heating to 65° C. for 15 minutes, yet stable at 45° C. Sodium dodecyl sulphate at a concentration of 0.1% does not inactivate this toxin thereby indicating extreme stability and thereby a protein which will fold into its appropriate form under a wide range of different conditions (which includes most cell types).

This new class of toxin may be purified by one or more methods of protein purification well known in the art. Insecticidal fragments may be generated from the purified toxin using, for example, cleavage with trypsin or cyanogen bromide.

As will be appreciated by those skilled in this field, the present invention provides a new class of toxins useful for genetically engineering a wide range of biological systems which will thus become more useful for control of insect pests detrimental to agricultural, aquatic and forest industries.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

TABLE 1

```
   1 AAGAAACCGT AACAGCGGAA ATCAACGCTG CAATTTATAT TAGTAGTCAT  SEQ ID NO:6
                                            Start         -35
  51 TTCAATAAAC GCCAACATAA TGGGAAAGTA CAATGGTTAT TAAACCCGTA
                     -10      S-D
 101 ACAACTCCGA GTGTAATACA ATTAACGCCT GATGATAGAG TAACGCCTGA
 151 TGATAAAGGT GAATATCAAC CCGTTGAAAA GCAAATAGCG GGAGATATAA
 201 TACGTGTACT AGAATTCAAG CAAACAAATG AAAGTCATAC AGGATTGTAT
 251 GGAATTCCAT ATCGAGCTAA GAAAGTAATA ATAGCATATG CTTTAGCGGT
 301 AAGTGGTATT CATAATGTCT CTCAACTTCC AGAAGACTAT TATAAAAATA
 351 AGGATAACAC AGGTAGAATT TATCAAGTAT ACATGTCTAA TCTTTTATCT
 401 GCACTATTGG GTGAGAATGG TGATCAAATT TCTAAAGATA TGGCAAATGA
 451 TTTTACCCAG AACGAACTGG AGTTTGAGGT CAACGTCTTA AAAATACCTG
 501 GGATATTCCT GATCTTGAGA ATAAACTATT GGAAGATTTA TTCAGATGAA
 551 GATAAATTAT TAGCACTATA TTTCTTTGCT TCACAAGAAC TTCCAATGGA
 601 GGCAAATCAA CAATCAAATG CAGCAAATTT TTTTAAAGTA ATTGATTTTT
 651 TACTTATCTT ATCTGCTGTA ACATCACTGG GAAAAAGGAT TTTTTCAAAA
 701 AATTTTTACA ATGGTCTAGA AACTAAATCA TTAGAGAATT ATATTGAGAG
 751 AAAAAAACTT TCTAAACCTT TCTTTCGACC ACCGCAGAAG TTACCTGATG
 801 GCAGAACAGG CTACTTGGCC GGTCCAACAA AAGCGCCTAA ATTGCCAACA
 851 ACGTCTTCTA CAGCAACAAC GTCTACAGCA GCTTCATCTA ATTGGAGAGT
 901 TAGTTTGCAA AAACCTTAGA GATAACCCAT CCAGAAATAC ATTTATGAAA
                          Stop
 951 ATGGATGATG CTGCAAAACG AAAATATAGT TCATTTATAA AAGAGGTACA
1001 AAAGGGTAAT GATCCACGTG CAGCAGCAGC AAGTATTGGT ACAAAAAGCG
1051 GCAGTAACTT CGAAAAACTG CAAGGTAGAG ATTTATATAG TATAAGACTA
1101 AGCCAAGAAC ACAGGGTAAC ATTCTCCATA AATAATACTG ACCAAATAAT
1151 GGAGATCCAA AGTGTTGGAA CTCATTACCA AAATATATAA CCTGATTTAT
1201 AGTAGTGATA AGACGTAAGA TAAATATGGA AGGTTGTAAT TCTATTGCAC
1251 TTCCTCAGAG GTGACCGCTC AG
```

TABLE 2

```
   1 MVIKPVTTPS VIQLTPDDRV TPDDKGEYQP VEKQIAGDII RVLEFKQTNE  SEQ ID NO:7
  51 SHTGLYGIPY RAKKVIIAYA LAVSGIHNVS QLPEDYYKNK DNTGRIYQVY
 101 MSNLLSALLG ENGDQISKDM ANDFTQNELE FEVNVLKIPG IFLILRINYW
 151 KIYSDEDKLL ALYFFASQEL PMEANQQSNA ANFFKVIDFL LILSAVTSLG
```

TABLE 2-continued

```
201 KRIFSKNFYN GLETKSLENY IERKKLSKPF FRPPQKLPDG RTGYLAGPTK

251 APKLPTTSST ATTSTAASSN WRVSLOKP*R *PIQKYIYEN G*CCKTKI*F

301 IYKRGTKG** STCSSSKYWY KKRQ*LRKTA R*RFI*YKTK PRTQGNILHK

351 *Y*PNNGDPK CWNSLPKYIT *FIVVIRRKI NMEGCNSIAL PQR*PL
```

We claim:

1. An isolated polynucleotide that encodes an insecticidal toxin of *Xenorhabdus nematophilus,* said polynucleotide comprising the nucleotide sequence of SEQ ID NO: 1 from base 1 to base 392.

2. The polynucleotide of claim 1, further comprising, at a position 3' of said nucleotide sequence, the second nucleotide sequence of SEQ ID NO: 1 from base 456 to base 830.

3. A purified insecticidal toxin from *Xenorhabdus nematophilus,* wherein said toxin is effective against *Galleria mellonella* larvae and comprises the amino acid sequence of SEQ ID NO: 2 from residue 1 to residue 131.

4. An isolated and purified expression vector comprising a promoter operatively linked to the nucleotide sequence of SEQ ID NO: 1 from base 1 to base 392.

5. The expression vector of claim 4, further comprising, at a position 3' of said nucleotide sequence, the second nucleotide sequence of SEQ ID NO: 1 from base 456 to base 830.

6. A bacterium or fungus transformed with the vector of claim 4.

7. A bacterium or fungus transformed with the vector of claim 5.

8. An infectious insect virus comprising the exogenous nucleotide sequence of SEQ ID NO:1 from base 1 to base 392, which nucleotide sequence is expressed upon infection of an insect cell.

9. The insect virus of claim 8, further comprising, at a position 3' of said nucleotide sequence, the second nucleotide sequence of SEQ ID NO: 1 from base 456 to base 830.

10. An isolated polynucleotide that encodes an insecticidal toxin from *Xenorhabdus nematophilus,* wherein said toxin kills *Galleria mellonella* larvae and comprises the amino acid sequence of SEQ ID NO: 2 from residue 1 to residue 131.

* * * * *